United States Patent
Lee

(10) Patent No.: US 6,641,694 B1
(45) Date of Patent: Nov. 4, 2003

(54) ANGIOPLASTY BALLOON WITH THIN-WALLED TAPER AND METHOD OF MAKING THE SAME

(75) Inventor: Jeong S. Lee, Diamond Bar, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/470,075

(22) Filed: Dec. 22, 1999

(51) Int. Cl.⁷ ............................................. B29C 49/22
(52) U.S. Cl. ............... 156/244.14; 264/512; 264/515; 264/516; 264/573
(58) Field of Search ............................ 264/515, 512, 264/516, 573; 156/244.14

(56) References Cited

U.S. PATENT DOCUMENTS

| | | |
|---|---|---|
| 3,694,280 A | 9/1972 | Hoef |
| 3,918,216 A | 11/1975 | Best et al. |
| 4,384,942 A | 5/1983 | Glowacki |
| 4,490,421 A | 12/1984 | Levy et al. |
| 4,551,292 A | 11/1985 | Fletcher et al. |
| 4,636,346 A | 1/1987 | Gold et al. |
| 4,952,357 A | 8/1990 | Euteneuer |
| 5,215,614 A | 6/1993 | Wijkamp et al. |
| 5,240,537 A | 8/1993 | Bodicky |
| 5,254,091 A | 10/1993 | Aliahmad et al. |
| 5,320,634 A | 6/1994 | Vigil et al. |
| 5,334,146 A | 8/1994 | Ozasa |
| 5,370,618 A | 12/1994 | Leonhardt |
| 5,378,237 A | 1/1995 | Boussignac et al. |
| 5,425,903 A | 6/1995 | Sloane, Jr. et al. |
| 5,456,666 A | 10/1995 | Campbell et al. |
| 5,556,383 A | 9/1996 | Wang et al. |
| 5,571,087 A | 11/1996 | Ressemann et al. |
| 5,587,125 A | * 12/1996 | Roychowdhury ........... 264/512 |
| 5,653,230 A | 8/1997 | Ciaglia et al. |
| 5,797,878 A | 8/1998 | Bleam |
| 6,045,547 A | 4/2000 | Ren et al. |

OTHER PUBLICATIONS

U.S. patent application Ser. No. 09/088,960, Bleam.

* cited by examiner

*Primary Examiner*—Suzanne E. McDowell
(74) *Attorney, Agent, or Firm*—Blakely, Sokoloff, Taylor & Zafman LLP

(57) ABSTRACT

An angioplasty balloon and method of manufacture are provided. The balloon has a working length and a taper each having a substantially equivalent thickness. This allows the balloon to be steered easily through vasculature to the site of a stenosis prior to inflation during an angioplasty procedure. The taper thickness in particular is achieved through use of a specially designed multi-tubular slug which is molded to form the angioplasty balloon of the present invention.

11 Claims, 2 Drawing Sheets

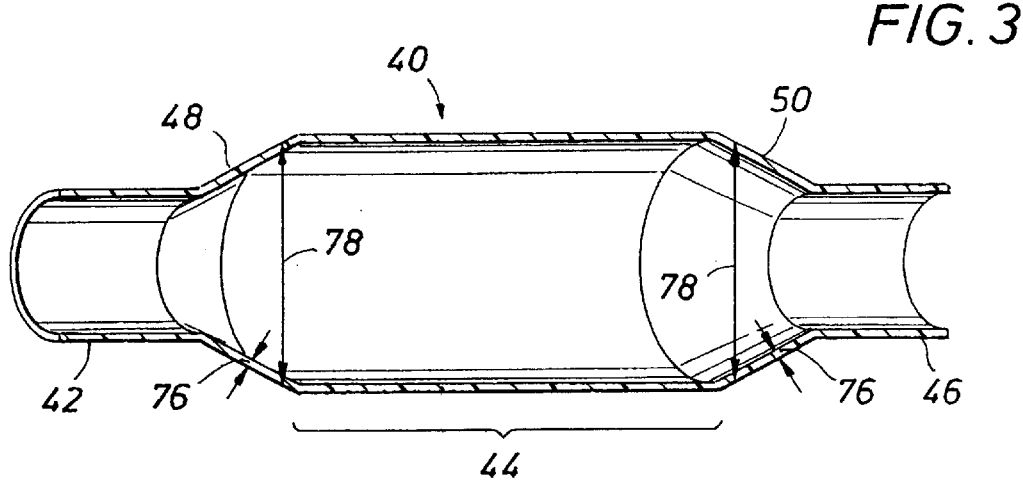

FIG. 3

```
┌─────────────────────┐
│ EXTRUDE INNER AND   │
│ OUTER TUBES         │
└─────────────────────┘
          │
          ▼
┌─────────────────────┐
│ OPTIONAL: PRE-NECK AN│
│ OUTER END OF SHORTENED│
│ OUTER TUBE          │
└─────────────────────┘
          │
          ▼
┌─────────────────────┐
│ FORM SLUG BY PLACING │
│ SHORTENED OUTER TUBE │
│ AROUND INNER TUBE    │
└─────────────────────┘
          │
          ▼
┌─────────────────────┐
│ PLACE SLUG WITHIN A  │
│ BALLOON MOLD         │
└─────────────────────┘
          │
          ▼
┌─────────────────────┐
│ MOLD SLUG INTO BALLOON│
│ BY ADDITION OF HEAT AND│
│ PRESSURE             │
└─────────────────────┘
```

FIG. 4

ANGIOPLASTY BALLOON WITH THIN-WALLED TAPER AND METHOD OF MAKING THE SAME

BACKGROUND OF THE INVENTION

1. Field of the Invention

This invention relates generally to dilation catheters. More particularly, the invention relates to intravascular angioplasty catheter balloons and a method of manufacturing the same.

2. Description of the Related Art

Angioplasty is a procedure by which stenotic lesions (atheromatous deposits), found in cases of atherosclerosis. During angioplasty, a guidewire is inserted into the cardiovascular system, generally via the femoral artery under local anesthesia. The guidewire is advanced through the patient's vasculature to the site of the stenosis (stenotic lesion). Placement of the guidewire may be aided by way of fluoroscopic observation. A dilatation catheter, having a guidewire lumen and distensible balloon portion, is then advanced through the vasculature until the balloon portion, at the distal end of the catheter, traverses or crosses a stenotic lesion. The artery is narrowed in the area of the stenotic lesion due to the atheromatous deposits occupying arterial space at the walls of the artery. Once placed, the balloon portion of the catheter is inflated, generally with a fluid, to compress the atheromatous deposits against the walls of the artery. This compression dilates the lumen of the artery leaving an unblocked arterial passage once the guidewire and catheter are removed.

Looking back to where the uninflated balloon encounters the stenosis, it must first cross at least a portion thereof in order to reach its distal-most destination. Therefore, a flexible, low profile balloon is preferable. In particular, the ends of the uninflated balloon should taper smoothly and lay low so that the balloon can be threaded into tight passages. It is preferable that the thickness of the balloon material be substantially constant from a working length throughout each taper. In the present context, a thick wall is at least approximately 0.002" in thickness while a thin wall is approximately 0.001" in thickness.

Unfortunately, current production methods yield a balloon with stiff and bulky tapers. These limitations are related to the behavior of the balloon material during manufacture, where a piece of polymer tubing is stretched to make the balloon. The balloon is made ("blown") by placing a segment of polymeric tubing in a mold, heating it to a near-molten state, and pressurizing the tubing until it fills the mold. The tubing within the mold forms the balloon. The mold is shaped such that the balloon is comprised of a working length with a taper at each end thereof. Each taper joins an unexpanded segment of tubing outside of the mold, referred to here as a shaft. Because the tapers expand less than the working length, they remain stiffer and bulkier. A thin-walled taper would be more desirable.

One approach to thinning the wall of the taper is a process called "pre-necking" in which the segment of tubing that will become the taper is first softened by heating and then subjected to a force which forms a narrowed segment in the tubing, referred to here as a neck. The objective of pre-necking is to form the taper from this neck. As the balloon is blown, the neck expands to form a taper having thinner walls than a taper blown from un-necked tubing. The thin taper terminates at a thin shaft. However, the problem of thick, stiff tapers still remains to a certain extent because the pre-necking is performed in a solid or semi-molten state in which the strain applied to the tubing induces crystallization. In effect, the molecular strands of the polymer become aligned parallel to the load inducing the strain. Once aligned in this manner, the polymer resists further distension. Thus, due to pre-necking, we have exchanged a thicker taper for a somewhat thinner taper which nonetheless remains less expansive than the reminder of the balloon. The remainder of the balloon, which is intended for contacting the wall of a body lumen such as during an angioplasty, is often referred to as the working distance or the working length. In the case of pre-necked balloons we end up with a thin taper which is less expansive than the working length.

What is needed, therefore, is an angioplasty balloon having a thin taper terminating at a thin shaft. It is desirable that the thin taper have a wall of substantially equivalent thickness to a wall of the working length.

SUMMARY OF THE INVENTION

It is an object of the present invention to provide an angioplasty balloon having a taper thickness substantially equivalent to a working length thickness.

It is an object of the present invention to provide an angioplasty balloon having a thin shaft.

It is an object of the present invention to provide an angioplasty balloon having a wall thickness no greater than 0.002", and in one embodiment between 0.0005" and 0.002".

It is an object of the present invention to provide a slug capable of being molded into an angioplasty balloon having a taper thickness substantially equivalent to a working length thickness.

It is an object of the present invention to provide a slug comprising a polymeric inner tube within a shortened polymeric outer tube.

It is an object of the present invention to provide a method of manufacturing an angioplasty balloon having a taper thickness substantially equivalent to a working length thickness.

In accordance with these objectives an angioplasty balloon 40 is provided having a taper wall thickness 76 substantially equivalent to a working length wall thickness 60. The angioplasty balloon 40 is manufactured from a slug 100 having an inner tube 106 within a shortened outer tube 102. The shortened outer tube 102 is fused to the inner tube 106 within a mold until an angioplasty balloon 40 has formed. The working length 44 of the angioplasty balloon 40 has formed from the shortened outer tube 102 while the inner tube 106 forms a taper (48, 50) at each end of the working length 44. Each taper (48, 50) terminates in a shaft (42, 46). The working length 44, taper (48, 50), and shaft (42, 46) each have substantially equivalent wall thicknesses (60, 66, 76).

BRIEF DESCRIPTION OF THE DRAWINGS

FIG. 3 is a side sectional view of the angioplasty balloon of the present invention.

FIG. 4 is a flow chart of a method of manufacturing the angioplasty balloon of the present invention.

DETAILED DESCRIPTION

Figure 1:
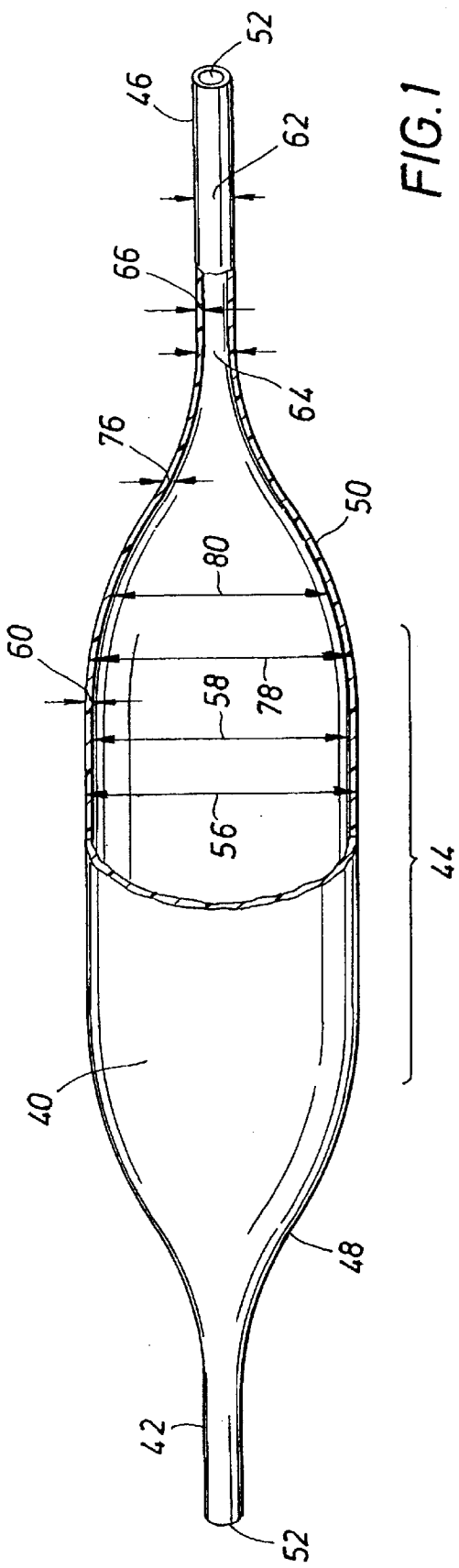
FIG. 1 is a perspective partially sectioned view of the angioplasty balloon of the present invention.

Referring to FIG. 1, the angioplasty balloon 40 of the present invention is shown partially sectioned. The angioplasty balloon 40 has a working length 44 which extends proximally into a proximal taper 48 and proximal shaft 42. The working length 44 extends distally into a distal taper 50 and distal shaft 46. A balloon lumen 52 is surrounded by the angioplasty balloon 40. The working length 44 has an inner diameter 58, an outer diameter 56, and a working length wall thickness 60 there between. The diameters (58, 56) are between 1.5 and 15.0 mm and fairly constant throughout the working length 44 of the angioplasty balloon 40. The working length wall thickness 60 is between 0.010 mm and 0.045 mm and fairly constant throughout the working length 44 of the angioplasty balloon 40.

Continuing with reference to FIG. 1, the distal shaft 46 has an inner shaft diameter 64, an outer shaft diameter 62, and a shaft wall thickness 66 there between. The diameters (64, 62) are between 0.600 mm and 0.720 mm and fairly constant throughout the distal shaft 46 of the angioplasty balloon 40. The shaft wall thickness 66 is between 0.010 mm and 0.051 mm and fairly constant throughout the distal shaft 46 of the angioplasty balloon 40. The length of the angioplasty balloon 40, between the distal shaft 46 and the proximal shaft 42, generally ranges from 10 mm to 40 mm. However, this is merely a matter of design choice. The proximal shaft 42 is fairly dimensionally equivalent to the distal shaft 46. However, the proximal shaft 42 is adaptable to communicating with an external supply of fluid pressure and/or delivering such to the angioplasty balloon 40.

The working length 44 adjoins the distal shaft 46 by way of a distal taper 50. The distal taper 50 has an inner taper diameter 80 and an outer taper diameter 78 which diminish from the working length 44 to the distal shaft 46 providing a smooth transition there between. A taper wall thickness 76 is found between the inner taper diameter 80 and the outer taper diameter 78. The proximal taper 48 is comparable to the distal taper 50 in dimensions and construction.

As configured for angioplasty, the angioplasty balloon 40 is affixed to the distal portion of a catheter (not shown). The balloon lumen 52 communicates with an inflation lumen of the catheter to provide inflation, fluid or otherwise, to the angioplasty balloon 40. When pressurized, tapers (48, 50) and the working length 44 expand until the full diameters (56, 58, 62, 64, 78, 80) are achieved. However, when not pressurized, tapers (48, 50) and the working length 44 lie flattened or folded. When the working length 44 is collapsed to its lowest profile, the tapers (48, 50) are able to collapse to a comparably low profile. Additionally, the flattened tapers (48, 50) have flexibility comparable to that of the flattened working length 44. These characteristics are advantageous because they lessen the resistance encountered by the uninflated balloon as it is forced through a tight stenosis or sharp curves of vasculature. As a result, the angioplasty balloon 40 can be maneuvered into more difficult stenoses and is less likely to traumatize the artery.

Figure 2:
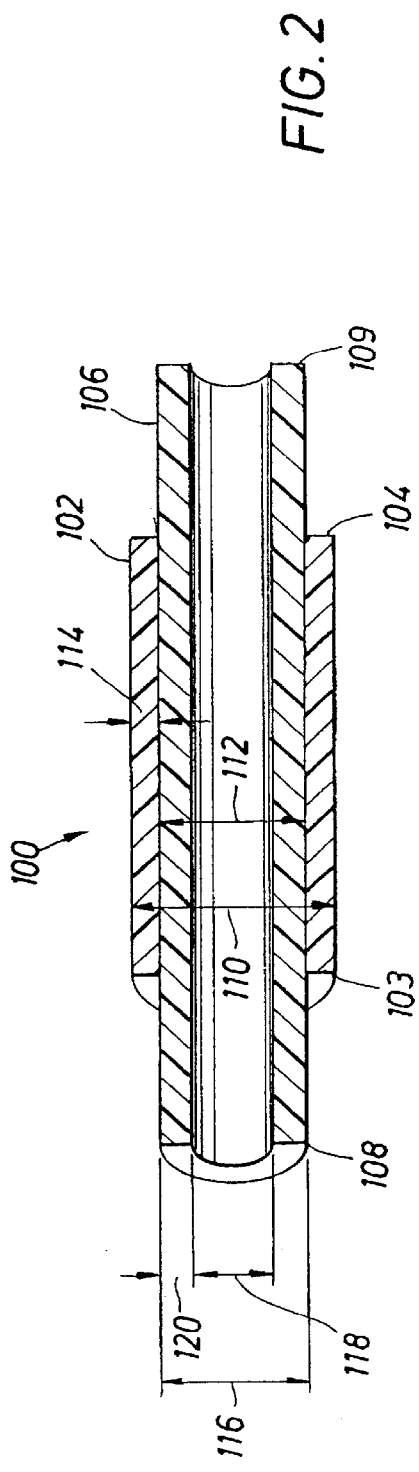
FIG. 2 is a side sectional view of the slug of the present invention.

Referring to FIG. 2, a cross sectional view of a slug 100 is shown. The slug 100 is made of a shortened outer tube 102 surrounding an inner tube 106 and being in communication therewith. The inner tube 106 has been inserted into the shortened outer tube 102. The shortened outer tube 102 has an outer proximal end 103 and an outer distal end 104. The shortened outer tube 102 has an outer tube outer diameter 110, an outer tube inner diameter 112 and an outer tube wall thickness 114 there between. The shortened outer tube 102 is of a length less than that of the inner tube 106. The inner tube 106 has an inner proximal end 108 and an inner distal end 109. The inner tube 106 has an inner tube outer diameter 112, an inner tube inner diameter 118 and an inner tube wall thickness 120 there between.

Referring to FIGS. 2–4, a cross sectional view of an angioplasty balloon 40 formed from the slug 100 is shown. The slug 100 has been placed within a mold (not shown) which defines a desired angioplasty balloon 40 profile. The slug 100 has been heated and pressurized, whereupon the shortened outer tube 102 and the inner tube 106 have filled the mold. During heating, the shortened outer tube 102 and the inner tube 106 have fused. During pressurization, the proximal taper 48 and the distal taper 50 have been formed by expansion of the inner tube 106 and the shortened outer tube 102 within the mold (not shown). Once the tapers (48, 50) have been formed in this manner, the angioplasty balloon 40 has been formed. In particular, the shortened outer tube 102 has formed the working length 44. The inner tube 106 and the outer distal end 104 have formed the distal taper 50. The inner tube 106 and the outer proximal end 103 have formed the proximal taper 48.

Continuing with reference to FIGS. 2–4, the tapers (48, 50) form easily as the angioplasty balloon 40 easily expands within the mold due to the configuration of the shortened outer tube 102 and the inner tube 106. This ease of expansion is due to the substantial disorientation of the molecular structure of the polymer compound of the tubes (102, 106). The tubes (102, 106) are extruded at molten temperatures hot enough to randomize the molecular alignment of the polymer. Generally, this randomization of molecular structure is followed by pre-necking which eliminates the randomization to a degree. However, the present invention provides a slug 100 which allows the reduction or complete elimination of pre-necking. With a reduction or elimination of pre-necking, little or no orientation is imposed upon the polymer and the tubes (102, 106) retain most, if not all, of their distensibility.

As a result of the configuration of the slug 100, less overall tube material is provided to the tapers (48, 50) than to the working length 44. This corresponds with the fact that the tapers (48, 50) occupy less overall space than the working length 44 in a formed angioplasty balloon 40. Thus, in the formed balloon 40, as the diameters (78, 80) of the tapers (48, 50) diminish from the working length 44 to the shafts (42, 46), the taper wall thickness 76 does not increase appreciably. Low profile and flexibility are achieved. This may be further enhanced by utilizing an inner tube wall thickness 120 less than the outer tube wall thickness 114. Additionally, having a larger diameter shortened outer tube 102 furthers a larger diameter working length 44, while a smaller diameter inner tube 106 furthers smaller diameter shafts (42, 46). These features contribute to low profile and flexibility of the angioplasty balloon 40.

The shortened outer tube 102 may be fused to the inner tube 106 before or during the formation of the angioplasty balloon 40 within the mold. Fusion prior to molding of the angioplasty balloon 40 may be achieved by various combinations of heat and pressure. Preferably, the temperature during fusion will exceed the glass transition temperature of the polymer. Above the glass transition temperature, the tubing is easily deformed. Below the glass transition temperature, the polymer resists deformation. Additionally, the tubes (102, 106) should be made of compatible materials, especially if fusion is to occur prior to the angioplasty balloon 40 being blown.

Generally, the tubes (102, 106) will be made from the same or compatible polymers. For example, both may be made of a polyetherblockamide material, commercially available as PEBAX® 7033 (PEBAX) or a like material, producing an angioplasty balloon 40 of uniform composition. Alternatively, the shortened outer tube 102 may be made of PEBAX while the inner tube 106 is made of a polyamide such as nylon. This will produce a two layer composite working length 44 having nylon shafts (42, 46). The use of a nylon inner tube 106 to produce a two layer composite working length 44 may provide an angioplasty balloon 40 capable of withstanding pressures higher than conventionally possible. If PEBAX-Nylon compositions are utilized where the tubes (102, 106) are fused while the angioplasty balloon 40 is blown, a high temperature (about 235° F.) and high pressure (300 p.s.i. or more) will be required.

Other combinations of materials include, for example, polyethylene terephthalate (PET) and a thermoplastic copolyester, commercially available as Hytrel® (a polyether-ester block copolymer) or Arnitel®. Thermoplastic copolyesters can be difficult to blow into a balloon shape because they lose their strength when heated. However, a composite of thermoplastic coplyester with PET (which readily forms a balloon shape) can produce a two layered angioplasty balloon 40. Alternatively, the tubes (102, 106) may be made of identical or different polyolefins.

In addition to the above variations, the slug 100 may be comprised of more than two tubes assembled together to achieve different shaft 42 or working length 44 properties. One of the tubes (102, 106, or another) may be a co-extruded tube of two or more layers. The slug 100 may or may not be pre-necked at its outer proximal end 103, its outer distal end 104, or both. Diameters (56, 58, 62, 64) may be constant or variable while the taper diameters (78, 80) may have identical or different characteristics as between the proximal taper 48 and the distal taper 50.

What is claimed is:

1. A method of forming an angioplasty,balloon catheter from a slug, said method comprising:

surrounding an inner tube with a shortened outer tube to form said slug;

placing said slug within a mold, said mold defining a desired angioplasty balloon profile; and molding said slug with said mold to form an angioplasty balloon catheter having a working length extending into a taper which further extends into a shaft, wherein said working length is formed from said shortened outer tube, and wherein at least a portion of said taper is formed from said inner tube.

2. The method of claim 1 further comprising adding an additional tube circumferentially around said inner tube prior to said molding.

3. The method of claim 1 wherein said molding further comprises:

heating said slug; and pressurizing said slug to form an angioplasty balloon within said mold, said angioplasty balloon comprising said working length and said taper.

4. The method of claim 3 wherein said heating further comprises providing a temperature above a glass transition temperature of any polymer comprising said slug.

5. The method of claim 3 wherein said pressurizing further comprises providing a pressure of at least 300 p.s.i. within said mold.

6. The method of claim 1 further comprising fusing said shortened outer tube to said inner tube prior to said molding.

7. The method of claim 6 wherein said fusing comprises heating said slug above a glass transition temperature of any polymer comprising said slug.

8. The method of claim 1 wherein said working length has a working length thickness, said taper has a taper thickness, and said shaft has a shaft thickness, said working length thickness, said taper thickness, and said shaft thickness being substantially equivalent.

9. A method of forming an angioplasty balloon catheter from a slug, said method comprising:

surrounding an inner tube with a shortened outer tube to form said slug;

placing said slug within a mold, said mold defining a desired angioplasty balloon profile;

molding said slug with said mold to form an angioplasty balloon catheter having a working length extending into a taper which further extends into a shaft; and extruding said inner tube and said shortened outer tube in a manner giving randomized molecular alignment to any polymer comprising said inner tube and said shortened outer tube prior to said surrounding.

10. A method of forming an angioplasty balloon catheter from a slug, said method comprising:

surrounding an inner tube with a shortened outer tube to form said slug;

placing said slug within a mold, said mold defining a desired angioplasty balloon profile;

molding said slug with said mold to form an angioplasty balloon catheter having a working length extending into a taper which further extends into a shaft; and pre-necking an outer end of said shortened outer tube prior to said molding.

11. A method of forming an angioplasty balloon catheter from a slug, said method comprising:

surrounding an inner tube with a shortened outer tube to form said slug;

placing said slug within a mold, said mold defining a desired angioplasty balloon profile;

molding said slug with said mold to form an angioplasty balloon catheter having a working length extending into a taper which further extends into a shaft, wherein said shortened outer tube further comprises an outer end, said molding transforming said shortened outer tube into said working length and said molding creating said taper from said outer end and said inner tube.

* * * * *